(12) United States Patent
Robinson et al.

(10) Patent No.: US 7,693,261 B2
(45) Date of Patent: Apr. 6, 2010

(54) METHOD AND APPARATUS FOR INSPECTION OF MATERIALS

(75) Inventors: Max Robinson, Shincliffe (GB); Arnab Basu, Belmont (GB)

(73) Assignee: Durham Scientific Crystals Limited (GB)

( * ) Notice: Subject to any disclaimer, the term of this patent is extended or adjusted under 35 U.S.C. 154(b) by 144 days.

(21) Appl. No.: 12/152,863

(22) Filed: May 16, 2008

(65) Prior Publication Data

US 2008/0283761 A1    Nov. 20, 2008

(30) Foreign Application Priority Data

May 17, 2007 (GB) ................................. 0709436.0
Sep. 8, 2007 (GB) ................................. 0717498.0

(51) Int. Cl.
*G01N 23/201* (2006.01)
(52) U.S. Cl. .......................................... 378/88; 378/57
(58) Field of Classification Search ............... 378/7, 378/57, 86–90
See application file for complete search history.

(56) References Cited

U.S. PATENT DOCUMENTS

| | | | |
|---|---|---|---|
| 5,265,144 A | 11/1993 | Harding et al. | |
| 5,943,388 A | 8/1999 | Tümer | |
| 6,018,562 A | 1/2000 | Wilson | |
| 6,118,850 A * | 9/2000 | Mayo et al. | 378/83 |
| 2008/0175350 A1 * | 7/2008 | MacDonald | 378/37 |
| 2009/0196397 A1 * | 8/2009 | Bertozzi et al. | 378/87 |

FOREIGN PATENT DOCUMENTS

| | | |
|---|---|---|
| EP | 0 496 454 A1 | 1/1992 |
| GB | 2 329 817 | 3/1999 |
| GB | 2 360 685 | 9/2001 |
| GB | 2 403 388 | 12/2004 |
| WO | WO 92/12415 | 7/1992 |

(Continued)

OTHER PUBLICATIONS

Measurement of the x-ray mass attenuation coefficient and the imaginary part of the form factor of silicon using synchrotron radiation; Tran et al.; The American Physical Society—Physical Review A 67, 042716 (2003) pp. 1-12.

(Continued)

*Primary Examiner*—Hoon Song
(74) *Attorney, Agent, or Firm*—Drinker Biddle & Reath LLP

(57) ABSTRACT

A method and apparatus for obtaining radiation transmission data including providing a radiation source, e.g., x-ray or gamma-ray source, and a radiation detector system, e.g., x-ray or gamma-ray detection system, spaced therefrom to define a scanning zone therebetween, the detector system capable of detecting and collecting spectroscopically resolvable information about incident radiation. Collecting a dataset of information about radiation incident including transmissivity of an object in the scanning zone at at least one scanning position from radiation transmitted through the object and received at the detector system. Resolving each dataset spectroscopically across a plurality of frequency bands within the spectrum of the source; at least one of the frequency bands corresponding to a characteristically scattered wavelength of a target species to be identified. The absence of or substantial reduction in a transmitted signal intensity at the frequency band is interpreted as the presence of the said target species.

21 Claims, 5 Drawing Sheets

FOREIGN PATENT DOCUMENTS

| WO | WO 2004/105610 | 9/2004 |
|---|---|---|
| WO | WO 2006/051445 | 5/2006 |

OTHER PUBLICATIONS

Hamamatsu; Energy Differentiation Type 64 CH, CdTe Radiation Line Sensor; C10413, Dated Aug. 2006, 4 pgs.

Pani et al: "Use of a novel controlled drift detector for diffraction enhanced breast imaging"; Nuclear Instruments & Methods in Physics Research, Section A: Accelerators, Spectrometers, Detectors and Associated Equipment, Elsevier, Amsterdam, NL, vol. 573, No. 1-2, Mar. 12, 2007, pp. 133-136, XP005921966, ISSN: 0168-9002.

Tran C Q et al: Absolute determination of the effect of scattering and fluorescence on x-ray attenuation measurements; Journal of Physics B, Atomic Molecular and Optical Physics, Institute of Physics Publishing, Bristol, GB, vol. 37, No. 15, Aug. 14, 2004, pp. 3163-3176, XP020054577, ISSN: 0953-4075, p. 3165-3166.

Kiyanagi et al.: "Material characterization using cold neutron transmission spectroscopy"; Physica B. Condensed Matter, Amsterdam, NL, vol. 385-386, Dec. 12, 2006, pp. 930-932, XP005781055, ISSN: 0921-4526.

Kiyanagi, Y. et al. "Some Experimental Studies on Time-of-Flight Radiography Using a Pulsed Neutron Source", IEEE Transactions on Nuclear Science, IEEE Service Center, New York, NY, US, vol. 52, No. 1, Feb. 1, 2005, pp. 371-374, XP011129958, ISSN: 0018-9499.

Kiyanagi Y et al., "Images obtained by neutron transmission measurement using time-of-flight method", Nuclear Instruments & Methods in Physics Research, section—A: Accelerators, Spectrometers, Detectors and Associated Equipment, Elsevier, Amsterdam, NL, vol. 542, No. 1-3, Apr. 21, 2005, pp. 316-319, XP004942991, ISSN: 0168-9002.

Suzuki Y et al.: "Discriminative imaging of local crystalline density and thickness variation in strained natural rubber by spectroscopic X-ray scattering topography", Japanese Journal of Applied Physics, Part 2 (Letters) Japan, vol. 34, No. 11A, Nov. 1, 1995, pp. L1503-L1505, XP002501371, ISSN: 0021-4922.

Santisteban J R et al.: "Engineering applications of Bragg-edge neutron transmission", Applied Physics A (Materials Science Processing) Springer-Verlag Germany, vol. A74, Dec. 2002, pp. S1433-S1436, XP002501370, ISSN: 0947-8396.

H.G. Priesmeyer, S. Vogel: "Bragg-edge transmission measurements" Mar. 6, 2006, pp. 180-181, XP002501369, Kiel, Germany, URL: http://www.ifg.uni-kiel.de/Veranstaltungen/kristallographie/1stKiel/abstracts/ab_vogel.ps.

Steuwer A et al.: "Using pulsed neutron transmisson for crystalline phase imaging and analysis", Journal of Applied Physics, American Institute of Physics, New York, NY, US, vol. 97, No. 7, Mar. 22, 2005, pp. 74903-1-74903-8, XP012071011, ISSN: 0021-8979.

Johnson R C et al.: High resolution powder diffraction by white source transmission measurements AIP Conference Proceedings USA, No. 89, 1982, pp. 53-55, XP002501368, ISSN: 0094-243X.

Dual energy detection of weapons of mass destruction; Paul J. Bjorkholm, Port Technology International; PT22-6/4; pp. 1-3 (Jun. 2005).

\* cited by examiner

2a

2b

METHOD AND APPARATUS FOR INSPECTION OF MATERIALS

FIELD OF THE INVENTION

This invention relates to a method and apparatus for the inspection and characterisation of material in three-dimensional space, especially by imaging.

BACKGROUND

The invention in particular relates to an apparatus and method making use of high energy radiation such as x-rays or gamma-rays to scan objects where it is desirable to gain information about their internal contents and/or composition. This principle is widely employed for example in the security industry, but might also be employed in other areas, for example, without limitation, medical imaging, imaging for quality control purposes or the purposes of determining the integrity of the structure, or the like.

X-Ray absorption has been used as the basis for screening objects to create some form of representational image of the contents or components thereof relative to each other in three-dimensional space. The thicker or more dense an object is then the more it will attenuate an x-ray beam. By use of suitable detectors and a suitable source, radiographs of an item under screening in the form of images based on the absorption of an object or set of objects can be generated.

Typically, an x-ray source generates an essentially 2-dimensional beam and detectors of transmitted x-rays are used to build up successive image slices in cross-section based on transmitted x-rays (and hence differentiating by absorption). A computer is used to generate images of cross-sections of the object so they can be looked at one at a time. The cross-sections are then put together to form an image reflecting at least some three-dimensional cues. It is for example known to employ a line-scan principle, in which three dimensional objects are caused to move through a scanning zone and imaging information collected as it moves and an image built up from successive linear slices. It is also for example known to employ a computed axial tomography (CAT or CT) principle in which an image is built up from a series of two-dimensional images taken around a single axis of rotation. The precise way that an image might be generated from transmitted radiation is not pertinent to the present invention.

These known apparatus and methods tend to give limited information about the material content. In essence, at its simplest, all that is being measured is transmissivity of the object to the source radiation. The detector merely collects amplitude information, and does not discriminate transmitted radiation spectroscopically. In most practical systems even this is measured indirectly. At its simplest, a typical linear array x-ray detector comprises in combination a scintillator material responsive to transmitted x-rays, which is then caused to emit lower frequency radiation, and for example light in or around the visible region, in combination with a semiconductor detector such as a silicon or gallium arsenide based detector which is responsive to this lower frequency radiation.

However, it is known that spectroscopic information from transmitted x-rays could be used to give additional information about the material content of the objects or components being scanned. It is known that the x-ray absorption properties of any material can vary spectroscopically, and that the amount by which the absorption properties vary depends in particular on atomic number. This has led to development of dual-band or dual-energy detectors which are capable of separately identifying low- and high-energy bands from the full spectrum of x-ray emissions. Such a dual-energy sensor typically comprises a sandwich pair of semiconductor photodiode rays or the like, in conjunction with a low-energy and a high-energy scintillator, such that the respective detectors detect transmission of low-energy and high-energy x-rays. The differential absorption effect is exploited by the dual energy detector to differentiate generally between objects having lower and higher atomic number elements predominating.

When exploited as part of a security or like material identification system, a very crude approximation can be made that organic materials tend to be in the former category and most inorganic materials in the latter category. The practical implications of this have led to the use of such detectors in the security industry, and for example in airport x-ray scanners, either to create separate images of metallic items inside luggage (to reveal hidden metal items and especially weapons, such as guns, and knives) or to identify plastic explosives.

Most explosives are dense organic materials usually high in nitrogen content. There is therefore some limited merit in the use of dual energy detectors but it is far from being a precise explosive detector since many other items in luggage, such as soaps, creams, leather goods etc, are also dense organic materials.

A dual energy system confers only limited information about composition. The organic/inorganic division is crude and approximate. Conventional detectors do not give any real spectroscopic information about the spectrum of transmitted x-rays although they detect the presence or otherwise of x-rays within two distinct bands of the spectrum. Ultimately decisions are made based on the attenuation radiograph which is based on the shape of items and their proximity to other objects.

Recent development of detectors that can resolve spectroscopic information about the transmitted X-rays more effectively has led to the development of apparatus that discriminate across a larger range of bands and generate a larger plurality of images. For example U.S. Pat. No. 5,943,388 describes a system that makes use of cadmium telluride detectors to image across at least three energy bands and generate at least three images. Hamamatsu Photonics KK has developed a line sensor system under model number C10413 that makes use of cadmium telluride detectors to image across five energy bands. These better exploit the effect of differential spectral absorption by different materials and enable a better approximation to be made between transmissivity and composition.

Even with this resolution, such devices can still be confused by objects which are superimposed in the x-ray path, and will give no information concerning the crystalline or polycrystalline nature of an object.

Polycrystalline materials scatter x-rays and, the resulting x-ray image may hardly detect such polycrystalline material because a very large proportion of the X-rays which have not been absorbed by the material will have been scattered and so not received by the detector. This is unfortunate as in security x-ray screening a number of threat items are polycrystalline in nature, in particular plastic explosives such as CP4, RDX, PETN and proprietary formulations thereof, drugs and the like and are therefore difficult to detect by using conventional x-ray systems.

Crystalline or polycrystalline objects are capable of diffracting an x-ray beam if certain conditions are satisfied.

The situation is outlined using Bragg's Law which is:

$$n\lambda = 2d \sin \theta$$

Where:
n is an integer (order of diffraction)
λ is the wavelength of the diffracted ray
d is the atomic lattice parameter
θ is the angle of diffraction At the specified wavelength (energy) the effect is close to 100%.

Attempts have been made to overcome detection problems associated with characteristic Bragg reflection by searching for the diffracted beam. If the threat material is specified then the information would be available concerning the diffraction angle θ0, the lattice parameter d, and the x-ray wavelength λ. In addition therefore, scanners have been proposed which make use of characteristic diffraction by including scatter detectors at appropriate scatter angles for particular target materials. Earlier patents GB2360685 and GB2329817 refer to just such an attempt. The energy of the diffracted photons is given by:

$$E_{ph} = \frac{hc}{\lambda}$$

where h is Planck's constant and c is the speed of light.

SUMMARY OF THE INVENTION

It is an object of the present invention to mitigate some or all of the above disadvantages of prior art scanning systems and methods.

It is a particular object of the present invention to provide a method and apparatus for x-ray scanning and preferably further for imaging of objects, and especially of containers of multiple objects or objects comprising multiple components, which provides additional information about their composition.

Therefore, according to one aspect of the invention there is provided a method of obtaining radiation transmission data, and preferably an image, of an object comprising the steps of:
providing a radiation source such as an x-ray or gamma-ray source and a radiation detector system such as an x-ray or gamma-ray detection system spaced therefrom to define a scanning zone therebetween, the detector system being capable of detecting and collecting spectroscopically resolvable information about incident radiation;
collecting a dataset of information about radiation incident at the detector and hence transmissivity of an object in the scanning zone at at least one and preferably a plurality of scanning positions, and preferably generating an image of an object in the scanning zone, and preferably a succession of images as the object moves through the scanning zone, from radiation transmitted through the object and received at the detector system;
resolving each such dataset or image spectroscopically across a plurality of frequency bands within the spectrum of the source;
wherein at least one of the said plurality of frequency bands corresponds to a characteristically scattered wavelength of a target species to be identified, and wherein the absence of or substantial reduction in a transmitted signal intensity at the frequency band is interpreted as the presence of the said target species.

The radiation source preferably comprises a source to deliver high-energy radiation such as ionizing radiation, for example high energy electromagnetic radiation such as x-rays and/or gamma rays, or subatomic particle radiation, and the detection system is adapted correspondingly to detect radiation in this spectrum. The radiation source for example is a broadband x-ray or gamma-ray source capable of producing broad spectrum emission over a wide range of x-ray or gamma-ray energies. Such a source will be familiar, and is widely used. The detector system is adapted to generate spectroscopic information about the transmitted radiation. That is, the detector exhibits a spectroscopically variable response across at least a part and preferably a substantial part of the spectrum of the radiation source allowing spectroscopic information to be retrieved. The detector system is capable of being used to detect quite specific frequency/energy bands, which term as used herein includes detection at effectively single discrete frequencies/energies. Instead of placing detectors at the appropriate positions to detect the diffraction beam angle θ of given energy $E_{ph}$, the detector system is used in accordance with the invention to show that the particular energy of interest is NOT there in the primary beam.

It has been noted that many target materials are crystalline or polycrystalline in structure. Such crystalline materials exhibit characteristic scattering of high energy electromagnetic radiation typically in the x-ray region. With conventional apparatus using a high energy electromagnetic source, and for example an x-ray source, this can present a problem. The primary beam might be scattered at these characteristic frequencies, making detection more difficult. However, where prior art systems treated this as a problem to be addressed by trying to detect the scattered secondary beams, the present invention takes a profoundly different approach, in that it seeks instead to detect absences in the primary beam.

This approach confers a number of advantages. Secondary scattered beams can be difficult to detect, requiring very precisely placed secondary detectors. The present invention dispenses altogether with the need for such secondary detectors. Instead, the primary detector system detects transmitted data in the primary transmitted beam and, by an appropriate numerical analysis technique, resolves this in such a way that characteristic scattering can be identified by the absence in the primary beam of a characteristic energy rather than by the presence of a secondary beam at a characteristic scatter angle.

Thus, in accordance with the method, for a given target species at least one frequency band is allocated which corresponds to a characteristic Bragg scattering condition. In particular, this might correspond to a first order Bragg scattering condition for a given target species, although additionally (for example to provide a confirmation) or alternatively a frequency band might be allocated to a characteristic lower order scattering.

The collected transmission data is resolved spectroscopically across the plurality of frequency bands. In the or each frequency band allocated to be characteristic of a given target species scattering occurs in accordance with Bragg's law at a characteristic energy within the frequency band, reducing the amplitude of the transmitted signal. If the frequency band is sufficiently narrow to correspond sufficiently closely to the characteristic scattering frequency a substantial and measureable reduction in transmitted amplitude will be resolved at the detector.

This reduction in amplitude over the specifically defined frequency band encompassing a characteristic scattering frequency, relative to the transmission data across the spectrum as a whole, is specifically characteristic of the target material, or at least characteristic of that class of materials having the same Bragg scattering properties as the target material. Thus, a characteristic absence or substantial reduction in a transmitted signal intensity in the primary transmitted beam at the frequency band may be interpreted as the presence of the said target species, and a result to that effect can be generated.

In practice, such a reduction in amplitude is determined numerically by comparison with the overall transmitted spectrum and/or by comparison with a known and for example prerecorded source spectrum. For example, from a known source intensity and a measured transmitted intensity across the overall transmitted spectrum a general extrapolated prediction can be made of the expected specific transmitted intensity across the overall energy spectrum, based on fitting the data to the standard exponential attenuation law. A numerical comparison of measured transmitted intensity versus extrapolated predicted transmitted intensity gives a numerical measure of reduction in amplitude at a target frequency, corresponding to a Bragg scattering condition for a target species. If this reduction for example exceeds a predetermined threshold level presence of the target species is considered identified.

It will be understood that although reference is made herein for convenience to the scanning of an object this should not be considered to limit the application of the invention to the scanning of single homogenous objects. Indeed, for many envisaged applications, an "object" is likely to consist of multiple heterogeneous materials and/or to be a container or other agglomeration of multiple articles, so that any transmitted radiation path is likely to pass through multiple different materials having varied properties. One of the particular advantages of the invention is that it can facilitate resolution of such varied materials.

The method of the invention is not limited in its application to the scanning and/or imaging of objects moving through a scanning zone in a scanner. Information pertinent to characteristic scattering inherent in the transmitted dataset for a given scanning event, and hence the material composition of an object or objects in a transmission path, can be obtained by a single scanning event, for example of a stationary object being scanned by a single beam of appropriate geometry, for example a pencil beam or conical beam. In such circumstance the method merely includes placing the object in a scanning zone to obtain such a single scan and single dataset of intensity data.

However, in a preferred embodiment information is collected regarding the transmissivity of an object under test in the scanning zone in a plurality of scanning positions between which the object is translated and/or rotated. In accordance with this embodiment of the method, the method comprises the additional step of causing an object to move relative to and for example through the scanning zone as a plurality of such datasets of intensity data are collected.

At its most basic, the invention allows identification of materials from collected and resolved transmission data based on a numerical analysis that provides, with reference to a suitable data library of characteristic scattering frequencies for at least one and preferably a range of target materials and/or objects likely to be encountered in a given application, an indication of material content. The data library may comprise information in any suitable form which can be related in a numerically analytical manner to data collected across the resolved energy band(s) in accordance with the invention. The data library may include standard preset reference materials and/or user input reference materials and/or reference data may be generated from known materials in accordance with the foregoing method. That is, a library of data may be built up by the system, which can in effect "learn" material characteristics, over time. The data library may comprise electronically stored data and/or data stored on a hard medium, such as a printed resource, and may be held and accessed locally and/or remotely, manually and/or automatically, none of which is directly pertinent to the operation of the method of the invention.

Thus, at its most basic, the invention allows identification of materials from collected transmission data based on characteristic reductions in amplitude at characteristic points in the spectrum. It need not generate an image. No particular transmission beam geometry is mandated. A simple, effectively one-dimensional beam geometry incident upon a simple, single detector may be sufficient.

However, for practical purposes it may be preferable that the invention forms part of and supplements the information offered by a scanning imaging system. In accordance with this preferred embodiment, the dataset of information about radiation incidence collected at the detector is used to generate an image of an object in the scanning zone. In particular, in a preferred mode of operation, a succession of images are generated, and each such image is resolved spectroscopically across a plurality of frequency bands within the spectrum of the source, at least one of which corresponds to a characteristically scattered frequency of a target species, and at least one of which is used to generate an image in conventional manner. More preferably, a plurality of frequency bands within the spectrum of the source are separately defined to correspond to a plurality of characteristic scatter frequencies, and a further plurality of frequency bands within the source are allocated to generate a series of energy-differentiated images, for example in a known manner by analogy with convention dual-energy or more fully differentiated imaging systems.

The method of the invention conveniently further provides the additional step of displaying such generated image or images, and in the case of multiple images might involve displaying such images simultaneously or sequentially.

For clarification it should be understood that where used herein a reference to the generation of image is a reference to the creation of information dataset, for example in the form of a suitable stored and manipulatable data file, from which a visual representation of the underlying structure of the object under investigation could be produced, and references to displaying this image are references to presenting an image generated from such a dataset in a visually accessible form, for example on a suitable display means.

The key to the invention is that the detector system can generate spectroscopic information about the transmitted radiation, and for example comprises an array one or more detectors that can generate spectroscopic information about the transmitted radiation. That is, the detector exhibits a spectroscopically variable response across at least a part of the radiation spectrum of the source allowing spectroscopic information to be retrieved.

Proper resolution of spectroscopic information confers two advantages. It offers the potential by imaging across a series of relatively broad bands to create several images which to some extent can reflect the different responses of materials and thus, by distinguishing between each image across each relatively broad band, for example by representing them differently (such as in different colours) in a resultant combined image, it assists in resolution of different objects, components or parts of the image. However, by also offering the potential to collect data across relatively narrow bands characteristic of Bragg scattering conditions for one or more given target crystalline species it can effect in accordance with the invention a genuine and much more specific identification of a target material or narrow class of materials.

So long as they are resolved, the exact bandwidth is not directly pertinent to the invention and useful results can be obtained by any suitable approach to dividing the spectrum, either in whole or in part, into separate bands. For example, the entire spectrum or a substantial part thereof may simply be divided between such a plurality of bandwidths, and each data item be considered as a measure representative of intensity across the entire band, and for example an average intensity. Alternatively, a plurality of relatively wide bands, but with discrete gaps therebetween, may be envisaged and analysed on the same basis. Alternatively, "bands" may be narrow even to the point where they essentially approximate to an evaluation of intensity at a single energy. As used herein the concept of intensity at an energy "band" includes evaluation of intensity at such a discrete single energy as well as evaluation of intensity at an energy across a narrow or broad bandwidth. Nevertheless, it is generally preferable that imaging bands are relatively broad and that characteristic bands are relatively narrow.

Similarly the source may be a single broad spectrum source across which a plurality of bandwidths or single energies may be identified. Alternatively or additionally sources may be provided having narrow bandwidths or generating incident radiation at one or more discrete energies to provide some of the energies for comparison in accordance with the method of the invention. In this case the radiation source is a plural source comprising a combination of sources at different energies to provide the necessary total spectrum spread to allow resolution by the detector across a plurality of energies/energy bands.

For example a plural source may comprise an x-ray source having a relatively lower energy spectrum, for example operating below 60 keV and for example at 10 to 50 keV and one or more other sources such as radioisotope sources generating radiation at higher energies, for example above 100 keV.

In accordance with a preferred embodiment of the invention, each collected image is resolved spectrospically across a plurality of frequency bands within the spectrum of the source comprising a plurality of relatively narrow "characteristic" frequency bands, each corresponding to and containing within the band a characteristic scatter frequency of a given target species, and/or a plurality of relatively broad "imaging" bands each intended to generate an image across a broader part of the overall spectrum, so that the imaging bands together allow the generation of an energy-differentiated composite image or succession of images. The number of characteristic frequency bands will be determined by the number of target species, and by whether a target species is mapped onto one or more than one characteristic scatter frequency. The number of imaging frequency bands is conveniently between 2 and 10, and for example between 4 and 8.

Spectroscopic detectors can be operated in an energy selective manner, giving rise to the ability to present an image resolved into a significantly increased number of "imaging" energy bands compared with the two that are available from standard prior art dual energy detectors. This information can be used to improve resolvability of objects of different composition.

This is achieved in accordance with this preferred embodiment in that spectroscopic resolution of transmitted radiation in each such relatively broad band is represented in the generated image. For example, spectroscopic differentiation in the collected data is represented in the image as differentiated colour, shading or marking. A banded mapping is used in that the source spectrum is divided into a plurality of bands, for example between four and eight bands, and different colours are used to represent each such band in the displayed image. The apparatus conveniently includes suitable image processing means to effect this mapping.

An image or composite image or succession of images so generated is preferably displayed on a suitable display means.

By analogy, in accordance with a further aspect of the invention there is provided an apparatus for scanning of and obtaining radiation transmission data from, and preferably an image of, an object comprising:

a radiation source and a radiation detector system spaced therefrom to define a scanning zone therebetween and to collect in use a dataset of information about radiation incident at the detector and hence transmissivity of an object in the scanning zone at at least one and preferably a plurality of scanning positions, and preferably to collect in use data for an image of an object in the scanning zone, and preferably a succession of images as the object is caused to move relative to the scanning zone;

a data processing apparatus to process and resolve each such dataset or image spectroscopically across a plurality of frequency bands within the spectrum of the source, wherein at least one of the said plurality of frequency bands corresponds to a characteristically scattered wavelength of a target species to be identified;

including a comparator to identify the absence of or substantial reduction in a transmitted signal intensity at the said frequency band and to output the same as an indication of the presence of the said target species.

Optionally, the apparatus is adapted to collect in use transmission intensity data with an object in a single scanning position and for example includes a means to retain an object in a scanning position such as a receptacle into which an object can be placed. Additionally or alternatively it may include a conveyor to convey an object into and out of such scanning position.

Optionally, the apparatus is adapted to collect in use transmission intensity data with an object in a plurality of scanning positions as the object moves relative to and for example through the scanning zone, and preferably to collect in use data for an image of an object in the scanning zone, and preferably a succession of images as the object moves through the scanning zone, in that it further comprises an object handler to cause an object to move relative to and for example through the scanning zone in use.

The apparatus of the invention has a data processing apparatus including a comparator to identify the absence of or substantial reduction in a transmitted signal intensity at the said frequency band and to output the same as an indication of the presence of the said target species. Any suitable form of c data processing apparatus combining suitable hardware and software and combining automatic and user-input calculation steps can be envisaged. For example the apparatus of the invention comprises a suitably programmed data processing apparatus such as a suitably programmed general purpose or special purpose computer.

It will be understood generally that a numerical step in the method of the invention can be implemented by a suitable set of machine readable instructions or code. These machine readable instructions may be loaded onto a general purpose computer, special purpose computer, or other programmable data processing apparatus to produce a means for implementing the numerical step specified, and in particular thereby to produce a calculation means as herein described.

These machine readable instructions may also be stored in a computer readable medium that can direct a computer or other programmable data processing apparatus to function in a particular manner, such that the instructions stored in a computer readable medium produce an article of manufacture including instruction means to implement some or all of the numerical steps in the method of the invention. Computer program instructions may also be loaded onto a computer or other programmable apparatus to produce a machine capable of implementing a computer executed process such that the instructions are executed on the computer or other programmable apparatus providing steps for implementing some or all of the numerical steps in the method of the invention. It will be understood that a step can be implemented by, and a means of the apparatus for performing such a step composed in, any suitable combinations of special purpose hardware and/or computer instructions.

Optionally, the apparatus further includes an image generation apparatus to generate at least a first image from the output of the detector system; and optionally further an image display adapted to display at least the first image.

The display means is conveniently a simple two dimensional display screen, for example a conventional video display screen (which term is intended to encompass any direct display or projection system exploiting any cathode ray tube, plasma display, liquid crystal display, liquid crystal on silicon display, light emitting diode display or like technology). It is a particular advantage that the method can be envisaged for use with, and the apparatus for the invention incorporated into, the standard display screens of comparable existing systems for example in the security or medical imaging fields.

The radiation source must produce a distribution of energies across a suitable spectral range for characteristic scattering, and is typically an x-ray source. Tungsten is the most appropriate target, but others could be used.

The source may be a single broad spectrum source across which a plurality of bandwidths (which term, as described above, encompasses herein single energies) may be identified. Alternatively or additionally sources may be provided having narrow bandwidths or generating incident radiation at one or more discrete energies to provide some of the energies for comparison in accordance with the method of the invention. In this case the radiation source is a plural source comprising a combination of sources at different energies to provide the necessary total spectrum spread to allow resolution by the detector across a plurality of energies/energy bands.

For example a plural source comprises an x-ray source having a relatively lower energy spectrum, for example operating below 60 keV and for example at 10 to 50 keV and one or more radioisotope sources generating radiation at higher energies, for example above 100 keV.

A detector system in accordance with the invention may comprise a single detector or a plurality of discrete detector elements making up a multi-element system. In particular for non-imaging applications operating an effectively zero-dimensional intensity only analysis a single detector may be preferred. For imaging applications a linear or area array may be preferred.

It is necessary that the detector system is enabled to detect radiation in a manner which is spectroscopically resolvable. Preferably, a detector system, or some or all discrete detector elements making up a multi-element system, is adapted to produce spectroscopic resolution in that it exhibits a direct spectroscopic response. In particular a system or element is fabricated from a material selected to exhibit inherently as a direct material property a direct variable electrical and for example photoelectric response to different parts of the source spectrum. For example, the detector system or element comprises a wide direct bandgap semiconductor material. For example, the detector system or element comprises a semiconductor material or materials preferably formed as a bulk crystal, and for example as a bulk single crystal (where bulk crystal in this context indicates a thickness of at least 500 μm, and preferably of at least 1 mm). The materials making up the semiconductor are preferably selected from cadmium telluride, cadmium zinc telluride (CZT), cadmium manganese telluride (CMT), germanium, lanthanum bromide, thorium bromide. Group II-VI semiconductors, and especially those listed, are particularly preferred in this regard. The materials making up the semiconductor are preferably selected from cadmium telluride, cadmium zinc telluride (CZT), cadmium manganese telluride (CMT) and alloys thereof, and for example comprise crystalline $Cd_{1-(a+b)}Mn_aZn_bTe$ where a and/or b may be zero.

Combination of these and any other such materials may be considered which give spectroscopic x-ray or other radiation detection rather than merely detecting amplitude of transmitted radiation and thus enable resolution at least of characteristic absences/amplitude reductions in the transmitted radiation indicating presence of a characteristic target species.

The apparatus includes a data processor to process the dataset and for example image data to resolve the data spectroscopically as above. The apparatus may include a data register in data communication with the dataset to store parameters for a frequency band, which may be preset or user-programmable. A data register may further store spectroscopic information about the source and a comparator may be provided to compare amplitude at a characteristic band with this source spectrum to identify characteristic absences.

As above described, each collected dataset and for example each collected image may be resolved spectroscopically across a plurality of frequency bands within the spectrum of the source comprising a plurality of relatively narrow "characteristic" frequency bands, each corresponding to and containing within the band a characteristic scatter frequency of a given target species, and/or a plurality of relatively broad "imaging" bands each intended to generate an image across a broader part of the overall spectrum, so that the imaging bands together allow the generation of an energy-differentiated composite image or succession of images in familiar manner.

An image generator may be provided to generate such an image. In particular it may be adapted to receive from the data processor a plurality of spectroscopically resolved images from a plurality of "imaging" bands and display these images successively or simultaneously to aid in object differentiation as above described. For example spectroscopic differentiation in the collected data is represented in a single combined image as differentiated colour, shading or marking.

The invention in particular relates to an apparatus and method operating on the line-scan principle, in which three dimensional objects are caused to move through a scanning zone and imaging information collected.

Imaging apparatus which employs the line-scan principle is well known. Typically, such apparatus will consist of an x-ray source, the beam of which may be collimated into a curtain, usually referred to as a "curtain beam", and is then detected by a linear array detector for example comprising a linear photodiode array. Image information is obtained by having the object of interest move linearly for example at right angles with respect to the beam and storing successive scans of x-ray transmission information derived from the linear array from which a complete image frame can be compiled.

Accordingly, in this embodiment, the method comprises:
providing an x-ray source and an x-ray detector system spaced therefrom to define a scanning zone therebetween, the detector system comprising at least one and preferably a plurality of linear array detectors capable of generating spectroscopically resolvable information about incident x-rays;

causing an object to move relative to and through the scanning zone; and resolving the resultant transmitted data in the manner above described.

Accordingly, in this embodiment, the apparatus comprises:

an x-ray source and an x-ray detector system spaced therefrom to define a scanning zone therebetween, the detector system comprising at least one and preferably a plurality of linear array detectors capable of generating spectroscopically resolvable information about incident x-rays.

In accordance with this embodiment the radiation source is preferably a curtain beam x-ray source as will be familiar from conventional line scan apparatus. The x-ray source may comprise a single primary source adapted to generate a beam such as a curtain beam aligned to be incident upon each linear detector in the laterally spaced serial array at a suitable angular separation, for example by a suitable beam splitting apparatus. A single beam may be generated. Alternatively, multiple beams may be generated from a single source. Alternatively, multiple sources may be provided each generating a beam such as a curtain beam incident upon a linear detector in the serial array. The x-ray source may comprise a source combining any or all of the foregoing principles.

In this embodiment an imaging system based on a spectroscopically resolving detector a number of broad energy bands could be selected to provide image and general materials identification whilst one or more could be set more narrowly to detect the ABSENCE of certain diffracted beam energies which would be characteristic of a threat item such as plastic explosive for example comprising PETN, RDX or formulations thereof.

If such an item were present it would certainly be large enough to affect many pixels in a line scan array. An important advantage is that it would be capable of detecting sheet explosive. This is a very real problem since there would probably be no shape information in the radiograph to indicate its presence.

In a practical situation, the line scan device could be set up to have prior knowledge of the x-ray spectrum from the x-ray source and so be able to recognise the almost complete absence of the particular narrow energy band during a normal screening pass.

BRIEF DESCRIPTION OF THE DRAWINGS

The invention will now be described by way of example only with reference to the accompanying drawings in which.

DETAILED DESCRIPTION OF THE EMBODIMENTS

Figure 1:
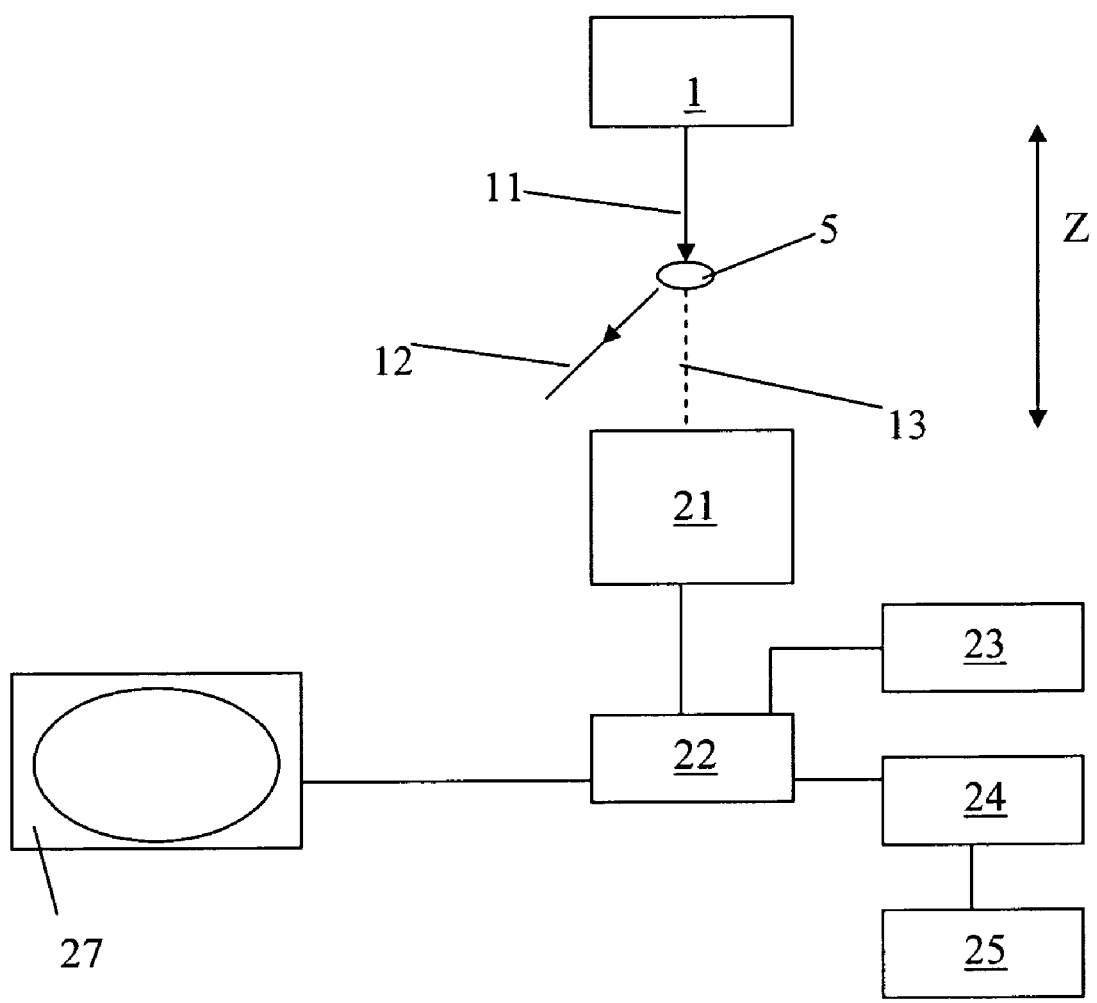
FIG. 1 is general schematic of a possible apparatus to implement the invention.

Referring first to the general schematic representation on FIG. 1, an x-ray source 1 and laterally spaced detector array 2 together define a scanning zone Z between them. In use, an object to be scanned is brought into and through the scanning zone in the usual manner, for example on a suitable conveyor belt (not shown).

In the illustrated example, a sample of crystalline material 5 sits in the scanning zone Z. An incident beam 11 from the x-ray source is illustrated. In the example, a diffracted beam 12 is diffracted at a characteristic angle in accordance with Bragg's law reducing the intensity of the transmitted beam 13 above and beyond the reduction which would be attributable to absorption alone. This illustrates the effect exploited by the invention.

The transmitted beam 13 is incident upon a detector array 21 which in a preferred embodiment comprises a plural linear array of cadmium telluride detector units.

The detector array 21 is in data communication with a processor 22. The detector array is used to generate a two dimensional "slice" in familiar manner. The inherent spectral resolution of the material in the array allows the processor 22 to resolve this image differentially across a plurality of pre-set frequency/energy bands in accordance with the principles of the invention by reference to energy band boundaries stored in the data register 23.

Figure 2:
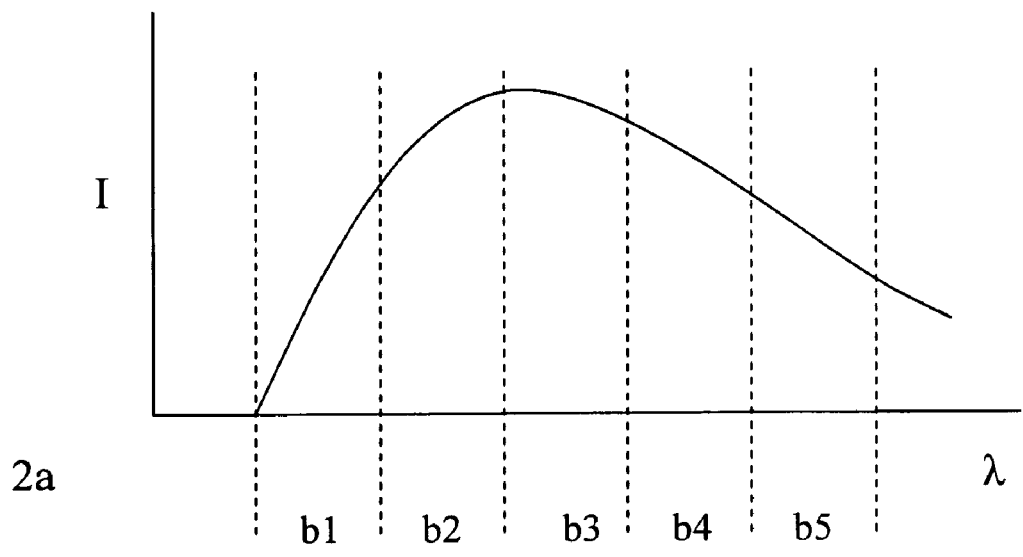
FIG. 2 illustrates a typical radiation source spectrum, and illustrates how it is partitioned to implement the invention.
Figure 2:
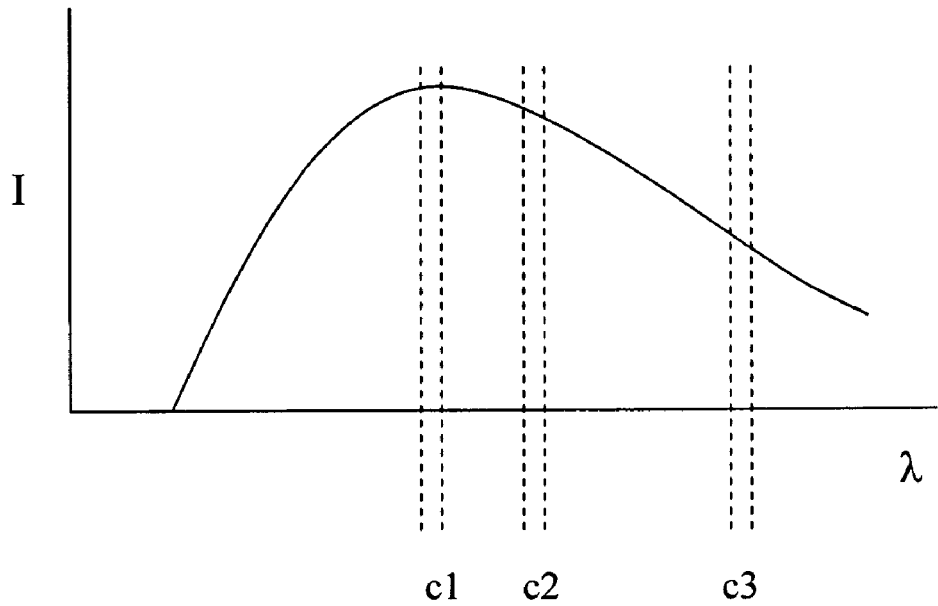
Figure 3:
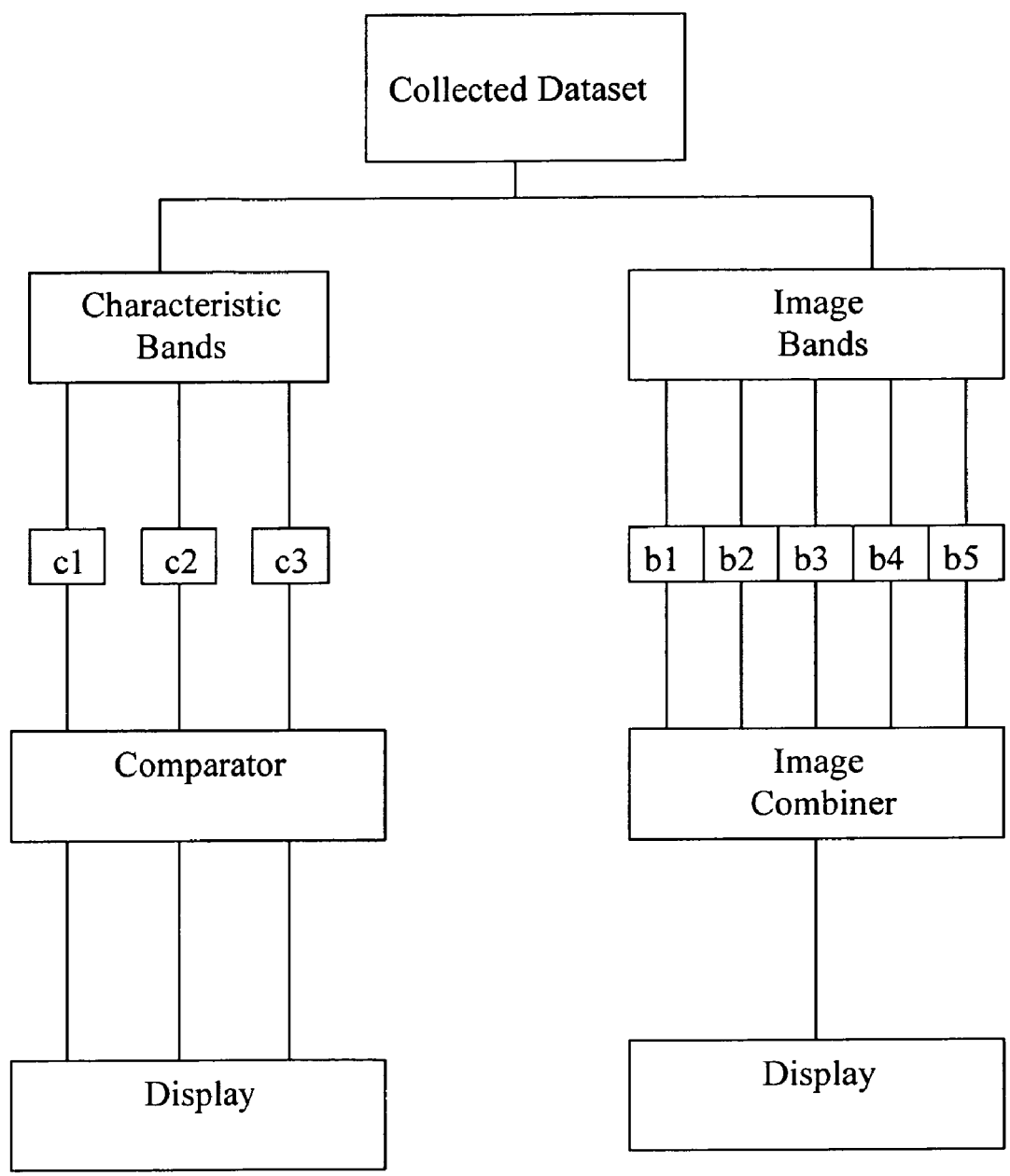
FIG. 3 is a schematic protocol for operation of the invention.

As is illustrated in more detail in FIGS. 2 and 3, some of these resolved energy bands are used to build up an energy-differentiated image for transmission to the display means 27. In this regard, the apparatus follows the same basic principles as conventional energy-differentiated imaging apparatus. It differs in the additional functionality provided by the comparator 24 which acts in relation to some of the identified frequency bands, each of which is associated with a characteristic Bragg scattering of a target species, to identify unusual reductions in the transmitted amplitude 13 within the characteristic frequency band which are indicative of characteristic scattering. This can be effected by comparison with a previously stored spectrum for the source 1 in the data register 25. The characteristically identified species may be identified to a user of the scanning system in any suitable way, either by inclusion in the image displayed on the display 27 or by another suitable alerting system. Any of the data processing or storage elements of the apparatus, for example including one or more of the processor 22, data register 23, comparator 24 and data register 25, may be provided by a suitably programmed data processor means such as a special purpose or general purpose computer.

The source 1 generates x-rays across a relatively broad spectrum of energy, so that this resolution may be exploited. It may be a plural source, or a single source with the necessary spread. The source 1 is preferably tungsten source, which gives a characteristic plot of x-ray intensity (I) versus wavelength ($\lambda$) as is illustrated in FIG. 2. FIG. 2 illustrates how this spectrum might be divided to operate a system in accordance with the principles of the invention. In FIG. 2a the overall spectrum is divided into successive relatively broad bands (b1 to b5). These are imaging bands h used to draw up a relatively conventional energy-differentiated image. In FIG. 2b the spectrum is additionally processed to target certain narrow frequency bands (c1 to c3). These are "characteristic" bands and each is associated with a characteristic Bragg scattering wavelength for a given target species. A given target species may have more than one characteristic band identified.

With the spectrum suitably resolved in the manner indicated in FIG. 2 by means of the processor 22 identified in FIG. 1 an image is generated and other, information retrieved in accordance with the flow chart process represented in FIG. 3.

Reading from top to bottom, the collected dataset is resolved both into the series of image bands and into the series of characteristic bands in the manner illustrated in FIG. 2.

Resolution of the image bands produces a series of images b1, b2, b3, b4 and b5 which together represent intensities of transmitted x-rays across relatively broad band widths but differentiated for energy for across the spectrum. In this way a degree of differentiation between objects of different composition is possible. Objects of different composition, and in particular a different atomic number, will tend to exhibit varying responses. If the different images b1 to b5 are for example successively displayed, or, more preferably, given distinctive colourations and displayed simultaneously in a single composite image, additional resolution of objects from the scan can be provided. This process is conventional in the art.

Where the invention notably differs is in the additional resolution of characteristic bands c1 to c3. These characteristic bands are relatively narrow, and each is intended to focus on and correspond to a characteristic Bragg scattering wavelength for a given target species. The resolved transmission data for these bonds in the register 25 are processed by a comparator to identify, for example with reference to a stored spectrum and/or with reference to intensity data in the vicinity of the characteristic band, any significant reduction in amplitude within the characteristic band suggestive of presence of characteristic scattering and hence of presence of the target species. The presence or absence so identified is then displayed, for example in combination with the complex image generated from the imaging band resolution or as an additional information display in association with the image or on a bespoke display.

In a preferred embodiment, the apparatus employs a line scan principle to generate an x-ray image. In airline security applications, the principle is encountered in particular in relation to hand baggage scanners. X-ray imaging might also be used in principle as a supplementary system for hold baggage (the reduced CT scan of the detection application being limited as regards imaging capability) but this is less common.

Figure 4:
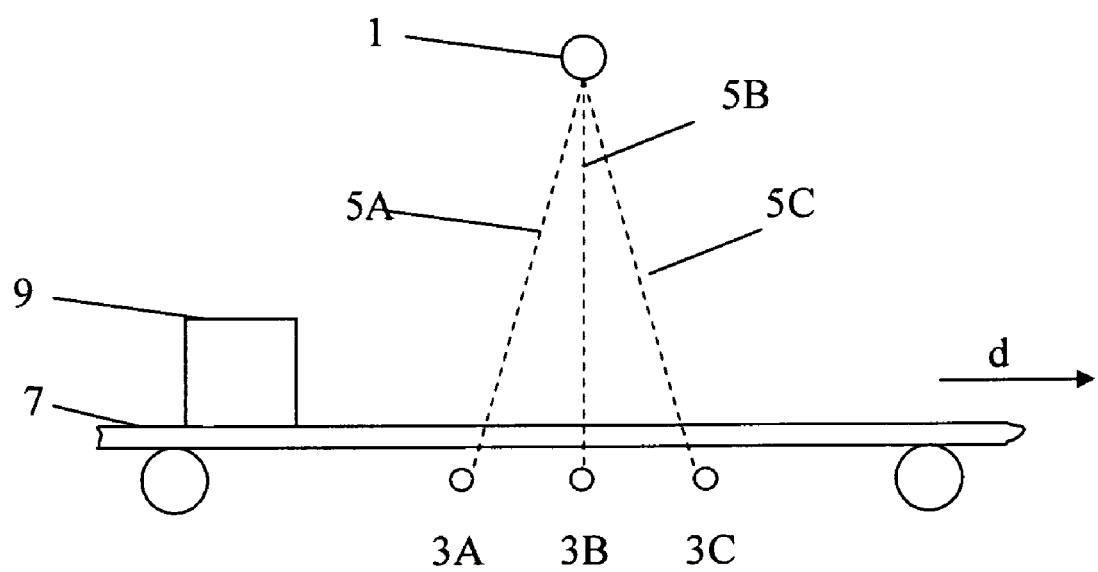
FIG. 4 is a side view of a simplified schematic representation of a scanning apparatus suitable for use in an embodiment of the invention.

FIG. 4 illustrates a suitable apparatus. The illustrated embodiment uses a single x-ray source collimated to produce a curtain beam incident upon the three linear detectors 3a to 3c (which in the embodiment each comprise a linear array of detector elements). Thus, a plurality of ray paths 5a to 5c are generated in the scanning zone by means of a plurality of curtain beams incident upon a linearly or angularly spaced array of such linear detectors. Incident ray paths 5a to 5c are shown through the scanning zone between the x-ray source 1 and, respectively, the detectors 3a to 3c.

In the embodiment, the linear array detectors 3a to 3c comprise material capable of spectroscopic resolution of incident x-rays, and in the specific example comprise cadmium telluride although the skilled person will appreciate that other material selections may be appropriate. To exploit this spectral resolution, the x-ray source emits x-ray across a broad energy spectrum. In the example a tungsten source is used, although the skilled person would appreciate that other materials might be appropriate.

An endless belt conveyor 7 causes an object to be scanned 9 to move in a direction d so as to intercept the ray paths 5a to 5c in the scanning zone. The envisaged application of this embodiment of the invention is as a security scanner, and object 9 can be considered typically to be a container that is expected to contain a variety of distinct objects which it would be useful and desirable to characterise compositionally and to view effectively in a third dimension (for example, an item of airline hold baggage). However, the skilled person would readily appreciate that the same principles can be applied for example to the scanning of objects for internal examination purposes, to medical scanning, and to similar applications.

Figure 5A:
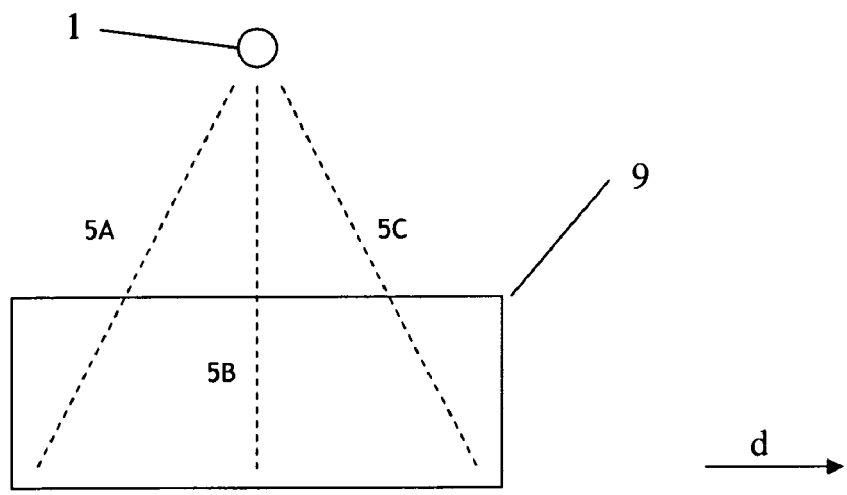
FIG. 5 illustrates the effect that can be created by images generated by means of the multiple ray paths provided by the embodiment of FIG. 4.

Datasets of transmitted intensity information are generated by building up transmitted information from each of the three detectors 3a to 3c. The processing of a dataset of information by resolving, at least to some extent, a relationship between incident energy/wavelength and transmitted intensity for both numerical analysis in accordance with the principles of the invention and spectroscopically resolved imaging purposes is carried out as above Although the invention, especially in non-imaging mode of operation, requires only a single ray path, the embodiment of FIG. 4 presents plural ray paths through an object. FIG. 5 illustrates an additional effect that can be created by images generated by means of the multiple ray paths provided by the embodiment of FIG. 4 which can further enhance the information provided.

Figure 5B:
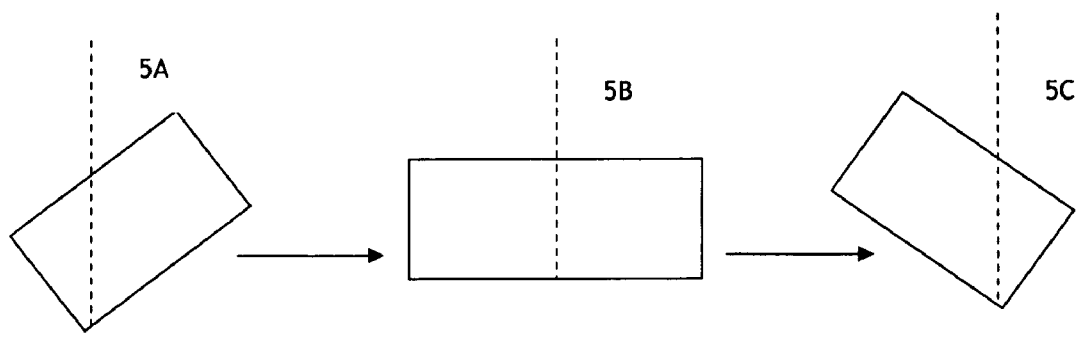

As an object 9 passes through incident ray paths 5a to 5c (see FIG. 5a) three images are generated in which the object is oriented differently relative to the x-ray source 1. Successive display of these images will cause the object to appear to rotate as is illustrated in FIG. 5b.

This ability in effect to get a view of the object which is in effect rotatable in a third dimension can be seen in some respects as analogous to CT scanning. In a conventional CT scanner, relative rotational movement between scanner and scanned object (usually, by orbital movement of the scanner) allows a rotatable image to be collected. The multiple image generated in this example offers some of these features as a result of the multiple ray paths provided by the apparatus, but with a less complex geometry, and for example on a simple linear conveyor such as is typically used in security scanning systems. This offers an additional image functionality.

In this way, in accordance with the invention, an apparatus and method is described which can offer specific material characterisation based on resolved energy detection and data processing to identify materials by the absence or reduction of characteristically scattered band. All this information is obtained from the primary transmitted beam by spectroscopic resolution and processing of the primary collected dataset and without the need for specific detection of characteristically scattered signals.

The invention claimed is:

1. A method of obtaining radiation transmission data of an object comprising the steps of:
    providing a radiation source and a radiation detector system spaced therefrom to define a scanning zone therebetween, the detector system being capable of detecting and collecting spectroscopically resolvable information about incident radiation;
    collecting a dataset of information about radiation incident at the detector and hence transmissivity of an object in the scanning zone at at least one scanning position from radiation transmitted through the object and received at the detector system; and
    resolving each such dataset spectroscopically across a plurality of frequency bands within the spectrum of the source;
    wherein at least one of the said plurality of frequency bands corresponds to a characteristically scattered wavelength of a target species to be identified, and wherein the absence of or substantial reduction in a transmitted signal intensity at the frequency band is interpreted as the presence of the said target species.

2. A method in accordance with claim 1 wherein at least one frequency band is allocated which corresponds to a characteristic first order Bragg scattering condition for a given target species.

3. A method in accordance with claim 1 wherein at least one frequency band is allocated which corresponds to a characteristic lower order Bragg scattering.

4. A method in accordance with claim 1 wherein a reduction in amplitude at a characteristic frequency band is determined numerically by comparison with the overall transmitted spectrum and/or by comparison with a known source spectrum and a result indicating the presence of the said target species is consequently generated.

5. A method in accordance with claim 1 wherein the dataset of information about radiation incidence collected at the detector is used to generate an image of an object in the scanning zone.

6. A method in accordance with claim 5 comprising the additional step of displaying a generated image or images.

7. A method in accordance with claim 5 wherein a succession of images is generated, and each such image is resolved spectroscopically across a plurality of frequency bands within the spectrum of the source, at least one of which corresponds to a characteristically scattered frequency of a target species, and at least one of which is used to generate an image.

8. A method in accordance with claim 7 wherein a plurality of frequency bands within the spectrum of the source are separately defined to correspond to a plurality of characteristic frequency bands, each corresponding to and containing within the band a characteristic scatter frequency of a given target species, and a further plurality of frequency bands within the source are allocated to generate a series of energy-differentiated images.

9. A method in accordance with claim 8 wherein the number of imaging frequency bands is between 2 and 10.

10. A method in accordance with claim 1 operating on the line-scan principle, comprising:
providing an x-ray source and an x-ray detector system spaced therefrom to define a scanning zone therebetween, the detector system comprising at least one linear array detector capable of generating spectroscopically resolvable information about incident x-rays;
causing an object to move relative to and through the scanning zone; and
resolving the resultant transmitted data.

11. An apparatus for scanning of and obtaining radiation transmission data from an object comprising:
a radiation source and a radiation detector system spaced therefrom to define a scanning zone therebetween and to collect in use a dataset of information about radiation incident at the detector and hence transmissivity of an object in the scanning zone at at least one scanning position;
a data processing apparatus to process and resolve each such dataset spectroscopically across a plurality of frequency bands within the spectrum of the source, wherein at least one of the said plurality of frequency bands corresponds to a characteristically scattered wavelength of a target species to be identified; and
a comparator to identify the absence of or substantial reduction in a transmitted signal intensity at the said frequency band and to output the same as an indication of the presence of the said target species.

12. An apparatus in accordance with claim 11 including a means to retain an object in and/or convey an object into and out of a scanning position.

13. An apparatus in accordance with claim 11 including an object handler to cause an object to move relative to and through the scanning zone in use.

14. An apparatus in accordance with claim 11 further including an image generation apparatus adapted co-operably with the detector to collect in use data for at least one image of an object in the scanning zone and to generate at least a first image from the output of the detector system.

15. An apparatus in accordance with claim 14 further including an image display means adapted to display at least the first image.

16. An apparatus in accordance with claim 11 wherein a detector is adapted to produce spectroscopic resolution in that it is fabricated from a material selected to exhibit inherently as a direct material property a direct variable electrical response to different parts of the x-ray spectrum.

17. An apparatus in accordance with claim 16 wherein the detector comprises a semiconductor material selected from a group consisting of cadmium telluride, cadmium zinc telluride (CZT), cadmium manganese telluride (CMT), germanium, lanthanum bromide, and thorium bromide.

18. An apparatus in accordance with claim 16 wherein the detector comprises a semiconductor material or materials formed as bulk crystal including a Group II-VI semiconductor material.

19. An apparatus in accordance with claim 18 wherein the detector comprises a semiconductor material selected from a group consisting of cadmium telluride, cadmium zinc telluride (CZT), and cadmium manganese telluride (CMT).

20. An apparatus in accordance with claim 11 operating on the line-scan principle, comprising:
an x-ray source and an x-ray detector system spaced therefrom to define a scanning zone therebetween, the detector system comprising at least one linear array detector capable of generating spectroscopically resolvable information about incident x-rays.

21. An apparatus in accordance with claim 20 wherein the radiation source is a curtain beam x-ray source.

* * * * *